(12) United States Patent
Ganan-Calvo

(10) Patent No.: US 7,059,321 B2
(45) Date of Patent: *Jun. 13, 2006

(54) DEVICE AND METHOD FOR CREATING AEROSOLS FOR DRUG DELIVERY

(75) Inventor: Alfonso Ganan-Calvo, Seville (ES)

(73) Assignee: Universidad de Sevilla, Seville (ES)

( * ) Notice: Subject to any disclaimer, the term of this patent is extended or adjusted under 35 U.S.C. 154(b) by 0 days.

This patent is subject to a terminal disclaimer.

(21) Appl. No.: 10/886,923

(22) Filed: Jul. 7, 2004

(65) Prior Publication Data

US 2005/0000512 A1    Jan. 6, 2005

Related U.S. Application Data

(63) Continuation of application No. 10/216,517, filed on Aug. 9, 2002, now Pat. No. 6,792,940, which is a continuation of application No. 09/191,317, filed on Nov. 13, 1998, now abandoned, and a continuation-in-part of application No. 09/171,518, filed as application No. PCT/ES97/00034 on Feb. 18, 1997, now Pat. No. 6,119,953.

(51) Int. Cl.
*A61M 11/00*    (2006.01)

(52) U.S. Cl. ............................. 128/200.22; 128/200.14

(58) Field of Classification Search ........... 128/200.14, 128/200.21, 200.22, 203.14, 203.25, 204.24, 128/204.25

See application file for complete search history.

(56) References Cited

U.S. PATENT DOCUMENTS

| | | | | |
|---|---|---|---|---|
| 173,194 A | * | 2/1876 | Wallace | 128/200.22 |
| 442,785 A | * | 12/1890 | Schoettl | 128/200.14 |
| 445,579 A | * | 2/1891 | Weldon | 128/200.14 |
| 3,700,170 A | | 10/1972 | Blanka et al. | |
| 3,804,255 A | | 4/1974 | Speece | |
| 4,141,055 A | | 2/1979 | Berry et al. | |
| 4,162,282 A | | 7/1979 | Fulwyler et al. | |
| 4,268,460 A | * | 5/1981 | Boiarski et al. | 128/200.21 |

(Continued)

FOREIGN PATENT DOCUMENTS

CH    563807    7/1975

(Continued)

OTHER PUBLICATIONS

Bowden et al., Science 276:233-5 (1997).

(Continued)

*Primary Examiner*—Aaron J. Lewis
(74) *Attorney, Agent, or Firm*—Karl Bozicevic; Bozicevic, Field & Francis LLP (57) ABSTRACT

A drug delivery device and method is disclosed which produces aerosolized particles of pharmaceutically active drug for delivery to a patient by inhalation. The device is comprised of a liquid feeding source such as a channel to which formulation is added at one end and expelled through an exit opening. The feeding channel is surrounded by a pressurized chamber into which gas is fed and out of which gas is expelled from an opening. The opening from which the gas is expelled is positioned directly in front of the flow path of liquid expelled from the feeding channel. Various parameters are adjusted so that pressurized gas surrounds liquid flowing out of the feeding channel in a manner so as to maintain a stable capillary microjet of liquid until the liquid exits the pressure chamber opening and is aerosolized. The aerosolized particles having a uniform diameter in the range of about 1 to 5 microns are inhaled into a patient's lungs and thereafter reach the patient's circulatory system.

15 Claims, 4 Drawing Sheets

U.S. PATENT DOCUMENTS

| | | | |
|---|---|---|---|
| 4,347,935 A | | 9/1982 | Merrill |
| 4,352,789 A | | 10/1982 | Thiel |
| 4,363,446 A | | 12/1982 | Jaeggle et al. |
| 4,444,961 A | | 4/1984 | Timm |
| 4,454,877 A | * | 6/1984 | Miller et al. ............ 128/203.14 |
| 4,603,671 A | | 8/1986 | Yoshinaga et al. |
| 4,617,898 A | | 10/1986 | Gayler |
| 4,628,040 A | | 12/1986 | Green et al. |
| 4,649,911 A | * | 3/1987 | Knight et al. ........... 128/200.21 |
| 4,662,338 A | | 5/1987 | Itoh et al. |
| 4,694,856 A | * | 9/1987 | Leibinsohn ............ 128/200.19 |
| 4,717,049 A | | 1/1988 | Green et al. |
| 4,781,968 A | | 11/1988 | Kellerman |
| 4,917,857 A | | 4/1990 | Jaeckel |
| 5,020,498 A | | 6/1991 | Linder et al. |
| 5,031,613 A | * | 7/1991 | Smith et al. ............ 128/200.21 |
| 5,077,176 A | | 12/1991 | Baggio et al. |
| 5,087,292 A | | 2/1992 | Garrido |
| 5,095,921 A | * | 3/1992 | Losee et al. ............ 128/200.19 |
| 5,174,247 A | | 12/1992 | Tosa et al. |
| 5,180,465 A | | 1/1993 | Seki et al. |
| 5,194,915 A | | 3/1993 | Gilby |
| 5,230,850 A | | 7/1993 | Lewis |
| 5,364,632 A | | 11/1994 | Benita et al. |
| 5,364,838 A | | 11/1994 | Rubsamen |
| 5,372,867 A | | 12/1994 | Hasegawa et al. |
| 5,397,001 A | | 3/1995 | Yoon et al. |
| 5,404,871 A | | 4/1995 | Goodman et al. |
| 5,458,292 A | | 10/1995 | Hapeman |
| 5,522,385 A | | 6/1996 | Lloyd et al. |
| 5,554,646 A | | 9/1996 | Cook et al. |
| 5,579,757 A | * | 12/1996 | McMahon et al. ...... 128/200.21 |
| 5,579,758 A | * | 12/1996 | Century ................. 128/200.22 |
| 5,597,491 A | | 1/1997 | Winkler |
| 5,697,341 A | | 12/1997 | Ausman et al. |
| 5,740,794 A | | 4/1998 | Smith et al. |
| 5,775,320 A | | 7/1998 | Patton et al. |
| 5,799,711 A | * | 9/1998 | Heinonen et al. ....... 128/200.19 |
| 5,884,846 A | * | 3/1999 | Tan ....................... 128/200.21 |
| 5,906,198 A | * | 5/1999 | Flickinger .............. 128/203.22 |
| 6,792,940 B1 | * | 9/2004 | Ganan-Calvo ......... 128/200.22 |

FOREIGN PATENT DOCUMENTS

| | | |
|---|---|---|
| DE | 4031262 A1 | 4/1992 |
| EP | 0 249 186 A1 | 12/1987 |
| EP | 0 250 164 A2 | 12/1987 |
| GB | 2255291 A | 11/1992 |
| GB | 2099078 A | 12/1992 |
| JP | 59174561 A | 10/1984 |
| JP | 03169331 | 7/1991 |
| WO | WO 90/05583 | 5/1990 |
| WO | WO 91/18682 | 12/1991 |
| WO | WO 94/11116 | 5/1994 |
| WO | WO 94/23129 | 10/1994 |
| WO | WO 95/23030 | 8/1995 |
| WO | WO 96/16326 | 5/1996 |
| WO | WO 97/43048 | 11/1997 |
| WO | WO 97/44080 | 11/1997 |

OTHER PUBLICATIONS

Brenn et al., *Chemical Engineering Science*, 52(2):237-244 (Jan. 1997) (Abstract).
Borchardt et al., *Chemistry & Biology*, 4(12):961-968 (1997).
Chin et al., *Trans. ASME J. Eng. Gas Turbines Power*, 106:639-644 (1983).
Cloupeau et al. (1989), *J. Electrostat* 22:135-159.
Fernández de la Mora et al. (1994), *J. Fluid Mech.* 260:155-184.
Forbes et al., *J. Austral. Math. Soc. Ser. B.*, 32:231-249 (1990).
Gañán-Calvo et al. (1997), *J. Aerosol Sci.* 28:249-275.
Gauthier, *Optics & Laser Technology*, 29(7): 389-399 (Oct. 1997).
Hartman et al. (1997), "Electrohydrodynamic Atomization in the Cone-Jet Mode," Paper presented at the ESF Workshop on Electrospray, Sevilla, Feb. 28-Mar. 1, 1997 [see also the papers contained in the Special Issue for Electrosprays (1994)].
Huck et al., *Journal of American Chemical Society* pp. 8267-8268 (1998).
Jasuja, *ASME Paper* 82-GT-32 (1982).
Liu et al. (1974), *J. Coloid Interface Sci.* 47:155-171.
Lorenzetto et al., *AIAA J.*, 15:1006-1010 (1977).
Nukiyama et al., *Trans. Soc. Mech. Eng. Jpn.*, 5:68-75 (1939).
Lord Rayleigh (1879), *Proc. London Math. Soc.* 10:4-13.
Service et al., (1997), *Science*, 277:1199-1200.
Singler et al., *Phys. Fluids A*, 5:1156-1166 (1993).
Tuck et al., *J. Austral. Math. Soc. Ser. B.*, 25:433-450 (1984).
Ünal, *Metall. Trans. B.*, 20B:613-622 (1989).
Whitesides et al., *Science* 254:1312-9 (1991).
Wigg, *J. Inst. Fuel*, 27:500-505 (1964).
Winfree et al., *Nature*, 394539-44 (1998).

\* cited by examiner

DEVICE AND METHOD FOR CREATING AEROSOLS FOR DRUG DELIVERY

CROSS-REFERENCES

This application is a continuation of application Ser. No. 10/216,517 filed Aug. 9, 2002 now U.S. Pat. No. 6,792,940 which is a continuation of application Ser. No. 09/191,317, filed Nov. 13, 1998, now abandoned and is a continuation-in-part of application Ser. No. 09/171,518 filed Apr. 21, 1999 now U.S. Pat. No. 6,119,953, which is a national phase filing of ES97/00034 under 35 USC §371 filed Feb. 18, 1997 now WO 97/43048, which claims priority of international application 9601101 filed May 13, 1996 under 35 USC §119 and also claims priority to P9702654 filed Dec. 17, 1997 under 35 U.S.C. § 119, all of which are incorporated herein by reference in their entireties and to which applications we claim priority under 35 USC §120 and 35 USC § 119.

FIELD OF THE INVENTION

This invention relates generally to the field of aerosols and more particularly to devices and methods for creating aerosols of pharmaceutical formulations for delivery to a human patient, preferably by inhalation.

BACKGROUND OF THE INVENTION

Aerosolizing formulations for inhalation has been considered as a convenient alternative to injection for decades. This alternative to injections is particularly interesting for drugs which cannot be delivered orally, e.g. insulin. Although most compounds will effectively move from the lungs into the circulatory system there is considerable unpredictability in how much aerosolized formulation reaches the areas of the lungs where the material can move into the circulatory system. This results in inefficiency and unpredictability of dosing. A number of devices have been proposed for improving the efficiency of aerosol delivery, monitoring patients and teaching patients to correctly use delivery devices.

There are several different types of devices which use generally different mechanisms and methodologies to produce aerosols for inhalation. The most commonly used device is a metered dose inhaler (MDI) which comprises a drug formulation container with the formulation including a low boiling point propellant. The formulation is held in the container under pressure and a metered dose of formulation is released as an aerosol when the valve on the container is opened. The low boiling point propellant quickly evaporates or "flashes" when the formulation is exposed to atmospheric pressure outside the container. The particles of formulation containing the drug without the propellant are inhaled into the patient's lungs and thereafter migrate into the patient's circulatory system. There are a number of different types of MDI devices. Devices of this type are disclosed in U.S. Pat. No. 5,404,871 issued Apr. 11, 1995 and U.S. Pat. No. 5,364,838 issued Nov. 15, 1994.

Another type of device is the dry powder inhaler (DPI) device. As indicated by the name such devices use formulations of dry powder which powder is blown into an aerosolized cloud via a burst of gas. Typical DPI devices are shown in U.S. Pat. No. 5,775,320 issued Jul. 7, 1998 and U.S. Pat. No. 5,740,794 issued Apr. 21, 1998.

Yet another type of aerosol delivery device forces a formulation through a porous membrane. Formulation moving through the pores breaks up to form small particles which are inhaled by the patient. Devices of this type are shown in U.S. Pat. No. 5,554,646 issued Aug. 13, 1996 and U.S. Pat. No. 5,522,385 issued Jun. 4, 1996.

Each of these devices has some advantages and disadvantages. The object of each is substantially the same—to repeatedly produce a fine mist aerosol wherein the particles are substantially uniform in size and within a size range of about 1 micron to about 5 microns. A patient can be accurately dosed if the device can repeatedly start with a given amount of formula and produce a known amount of aerosol with particles having sizes within a known range. The present invention endeavors to provide a device and method for obtaining accurate repeatable dosing of a patient with an aerosol.

SUMMARY OF THE INVENTION

Aerosolized particles within a desired size range (e.g., 1 micron to about 5 microns) are produced from a liquid formulation comprised of a pharmaceutical active drug and a carrier. The particles produced all have substantially the same particle diameter ±3% to ±30%, e.g. all particles in the aerosol have a diameter of 2 microns ±3% to ±10%. The formulation is provided in any desired manner (e.g., forced through a channel of a feeding needle and expelled out of an exit opening of the needle). Simultaneously, gas contained in a pressure chamber (which surrounds at least the area where the formulation is provided, e.g., surrounds the exit opening of the needle) is forced out of an opening positioned in front of the formulation, e.g., directly in front of the flow path of the formulation being expelled from the feeding needle. Various parameters are adjusted to obtain a super critical flow of liquid characterized by a stable liquid-gas interface and a stable capillary jet of the liquid which forms particles on exiting the opening of the pressurized chamber which particles will all (90% or more) have substantially the same diameter, i.e., a monodisperse aerosol.

An object of the invention is to provide a device for aerosolized delivery of a pharmaceutically active drug formulation or a diagnostic formulation.

Another object is to provide a method of creating an aerosol of consistent particle size (±3 to 30% or preferably ±3 to 10% difference in diameter) which aerosol is inhalable by a patient for aerosolized delivery of drugs or diagnostics.

A feature of the invention is that the diameter of the opening from which liquid is expelled, the diameter of the opening from which gas is expelled and the distance between these two openings is adjustable and is adjusted to obtain a stable liquid-gas interface which results in a stable capillary microjet being formed by the liquid expelled which microjet is focused on an exit opening by the flow of surrounding gas.

Another feature of the invention is that the viscosities and velocities of the fluids can be chosen with consideration to other adjusted parameters to obtain a supercritical flow of liquid.

Another feature of the invention is that the liquid can be a single liquid, two or more (miscible or immiscible) liquids mixed, a solution or a suspension.

An advantage of the invention is that the gas flowing with the particles prevents the particles from agglomerating thereby maintaining a monodisperse aerosol.

An advantage of the invention is that it consistently produces aerosols having particles with a desired particle diameter e.g. 1 to 5 microns.

An advantage of the invention is that the device of the invention is energy efficient in terms of the energy used to create small particles for inhalation.

Another advantage is that the structure of the device and its use are simple.

Another advantage is that clogging of the exit opening of the pressure chamber is substantially eliminated because liquid is kept out of contact with the surface of the exit opening by a surrounding focused funnel of gas which flows out of the pressure chamber exit opening.

Yet another advantage is that particles produced are substantially smaller in size than would be expected based on the diameter of the exit opening of the pressure chamber due to focusing the flow of the liquid with the flow of surrounding gas.

An aspect of the invention is a hand-held, self-contained portable drug delivery device which consistently produces small aerosolized particles which are relatively uniform in size.

Another aspect of the invention is a device and method which produces multiple streams of aerosol thereby quickly aerosolizing a large dose of formulation for inhalation by a patient.

These and other aspects, objects, features and advantages will become apparent to those skilled in the art upon reading this disclosure in combination with the figures provided.

BRIEF DESCRIPTION OF THE DRAWINGS

FIG. 3 is a schematic view of yet another embodiment showing a wedge-shaped planar source of formulation.

DETAILED DESCRIPTION OF PREFERRED EMBODIMENTS

Before the present aerosol device and method are described, it is to be understood that this invention is not limited to the particular components and steps described, as such may, of course, vary. It is also to be understood that the terminology used herein is for the purpose of describing particular embodiments only, and is not intended to be limiting, since the scope of the It must be noted that as used herein and in the appended claims, the singular forms "a", "and," and "the" include plural referents unless the context clearly dictates otherwise. Thus, for example, reference to "a particle" includes a plurality of particles and reference to "a fluid" includes reference to a mixture of fluids, and equivalents thereof known to those skilled in the art, and so forth. present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "formulation" is used to describe any single liquid, mixture, solution, suspension or the like which is a flowable liquid at room temperature and comprises either a pharmaceutically active compound, a diagnostic compound or a compound which becomes an active compound after entering a patient, e.g. prodrugs or DNA encoding proteins. The formulation is preferably further comprised of a carrier and more preferably is a liquid that has physical properties (e.g., viscosity) such that when the formulation is moved through a device of the invention the formulation is aerosolized into particles (0.1 to 10 microns in diameter) which are inhaled into the lungs of a patient and preferably reach the circulatory system. The carrier may be any pharmaceutically acceptable material and is preferably a flowable liquid which is compatible with the active agent. Formulations are preferably solutions, e.g., aqueous solutions, ethanolic solutions, aqueous/ethanolic solutions, saline solutions, colloidal suspensions and microcrystalline suspensions. Formulations can be solutions or suspensions of drugs (including systemically active drugs, e.g. insulin, insulin analogs including monomeric insulin such as insulin lispro) in the above mentioned liquids.

The term "carrier" shall mean a substantially inactive (biologically) component of a formulation such as a pharmaceutically acceptable excipient material which an active ingredient such as a drug, a diagnostic agent, prodrug or a gene vector is mixed with, suspended or dissolved in. The carrier is preferably a flowable liquid. Useful carriers do not adversely interact with the drug, diagnostic or gene vector and have properties which allow for the formation of aerosolized particles preferably particles having a diameter in the range of 0.1 to 10.0 microns (more preferably 1 to 5 microns) when a formulation comprising the carrier and active ingredient is aerosolized out of a device of the invention. Carriers include water, ethanol, saline solutions and mixtures thereof with pure water being preferred. Other carriers can be used provided that they can be formulated to create a suitable aerosol and do not adversely effect the active component or human lung tissue.

The term "active compound" means a compound which is either a pharmaceutically active drug, becomes or produces a therapeutic compound in the body or is a detectably labeled compound. In turn, a "pharmaceutically active drug"

or therapeutic compound shall be interpreted to mean any pharmaceutically effective compound used in the treatment of disease. A "detectably labeled compound" includes compounds which are radioactively labeled see U.S. Pat. No. 5,829,436 issued Nov. 3, 1998 Re: detectable labels.

Pharmaceutical formulations for use in the invention may be comprised of any therapeutic agent that can be atomized for patient delivery, e.g. for pulmonary delivery using an inhalation delivery system. Examples of such pharmaceutical compositions may be found in the Physicians Desk Reference (1998), and Remington: The Science and Practice of Pharmacy 19$^{th}$ Edition (1995), both of which are incorporated herein by reference. These formulations may be in any form capable of atomization, such as a solution, a suspension, an emulsion, a slurry, etc., provided the dynamics of the form render it capable of forming a capillary microjet upon exposure to a second fluid.

The terms “electronic particle sensing device” and “electronic detection system” refer to a device or other means for measuring and counting particles present in an aerosol mist.

The term “reporting means” is used herein to indicate a means by which information obtained from a monitoring device such as an electronic particle sensing device or a device which monitors and records information relating to the patient’s respiratory movement, may be provided to the user.

The term “aerosol bolus” is used herein to describe a volume of air greater than 50 ml and less than 4 liters which has suspended within it particles of a formulation wherein the particles have a diameter in the range of 0.1 to 10 microns, preferably 1 to 5 microns, and preferably the total volume of formulation is from 5 μl to 10,000 μl. About 10 μl of particles having a diameter of about 1 to 3 microns are present in a volume of about 50 ml to 2 liters, preferably 100 ml to 1,000 ml.

The term “aerosol” means any part of an aerosol bolus as described above.

The terms “air”, “particle free air”, “aerosol free air,” and the like, are used interchangeably herein to describe a volume of air which is substantially free of other material and, in particular, free of particles intentionally added such as particles of formulation which create the aerosol. The term means that the air does not include particles of formulation which have been intentionally added but is not intended to imply that the normal surrounding air has been filtered or treated to remove all particles although filtering can take place. Air is the preferred gas to use with drug delivery it being noted that other non-toxic gases, e.g., $CO_2$ can be used.

The term “measuring” describes an event whereby the (1) total lung capacity, (2) inspiratory flow rate or (3) inspiratory volume of the patient is measured and/or calculated. The information is preferably used in order to determine an optimal point in the inspiratory cycle at which to release an aerosol and/or a particle free volume of air. An actual measurement of both rate and volume may be made or the rate can be directly measured and the volume calculated based on the measured rate. The total lung capacity can be measured or calculated based on the patient’s height, sex and age. It is also preferable to continue measuring inspiratory flow during and after aerosol delivery and to record inspiratory flow rate and volume before, during and after the release of formulation. Such reading makes it possible to determine if aerosolized formulation was properly delivered to the patient.

The term “monitoring” event shall comprise determining the character of an aerosol such as the size, number and speed of the particles in the aerosol, further, monitoring may comprise measuring lung functions such as inspiratory flow, inspiratory flow rate, and/or inspiratory volume so that a patient’s lung function as defined herein, can be evaluated during before and/or after delivery thereby making it possible to evaluate the effect of formulation such as respiratory drug delivery on the patient’s lung function.

The term “inspiratory flow rate” shall mean a value of air flow rate determined, calculated or measured based on the speed of the air passing a given point in a measuring device assuming atmospheric pressure ±5% and a temperature in the range of about 110° C. to 40° C.

The term “inspiratory flow” shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term “inspiratory volume” shall mean a determined, measured or calculated volume of air passing a given point into the lungs of a patient assuming atmospheric pressure ±5% and a temperature in the range of 10° C. to 40° C.

The terms “lung function” and “pulmonary function” are used interchangeably and shall be interpreted to mean physically measurable operations of a lung including but not limited to (1) inspiratory and (2) expiratory flow rates as well as (3) lung volume, i.e., total lung capacity. Methods of quantitatively determining pulmonary function are used to measure lung function. Quantitative determination of pulmonary function may be important when delivering any formulation and in particular respiratory drugs in order to direct the aerosol to a specific area of the lung and to determine effectiveness. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient’s pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering formulation in a delivery event and monitoring lung function in a monitoring event. A series of such events may be carried out and repeated over time to determine if lung (see U.S. Pat. No. 5,404,871) function is improved.

Each of the parameters discussed above is measured during quantitative spirometry. A patient’s individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The terms "particles", "aerosolized particles" and "aerosolized particles of formulation" are used interchangeably herein and shall mean particles of formulation comprised of any pharmaceutically active ingredient, a compound which becomes such in the body (e.g. a prodrug or DNA encoding a protein) or a diagnostic compound. Any of these is preferably with a carrier, (e.g., a pharmaceutically active respiratory drug and carrier). Particles of a liquid formulation are formed upon forcing the formulation from anywhere it is provided (e.g., the feeding needle) and then out of the pressure chamber exit orifice. The particles have a size which is sufficiently small such that when the particles are formed they remain suspended in the air for a sufficient amount of time such that the patient can inhale the particles into the patient's lungs. The particles have a size in the range of 0.1 micron to about 10 microns, preferably 1 to 5 microns. Particle diameter is an aerodynamic diameter.

In referring to particle diameter, the diameter measurement given is the "aerodynamic diameter" measurement which is the diameter of a sphere of unit density that has the same terminal sedimentation velocity in air under normal atmospheric conditions as the particle in question. This is pointed out in that it is difficult to accurately measure the diameter of small particles using current technology and the shape may be continually changing. Thus, the diameter of one particle of material of a given density will be said to have the same diameter as another particle of the same or a different material if the two particles have the same terminal sedimentation velocity in air under the same conditions.

Device in General

The present disclosure focuses on the use of an aerosol creation device to produce aerosolized liquid formulations for delivery of drugs to patients—preferably by inhalation into the lungs.

The basic technology of the invention comprises (1) a means for supplying a first fluid; and (2) a pressure chamber supplied with a second fluid. The first fluid is generally a liquid and preferably aqueous. The second fluid is generally a gas and preferably air. However, the first fluid may be a gas and second fluid a liquid or both fluids may be liquid provided the first and second fluid are sufficiently different from each other (immiscible) so as to allow for the formation of a stable microjet of the first fluid moving from the supply means to an exit port of the pressure chamber. Notwithstanding these different combinations of gas-liquid, liquid-gas, and liquid-liquid the invention is generally described with a liquid formulation being expelled from the supply means and forming a stable microjet due to interaction with surrounding air flow focusing the microjet to flow out of an exit of the pressure chamber.

Formation of the microjet and its acceleration and ultimate particle formation are based on the abrupt pressure drop associated with the steep acceleration experienced by the first fluid (e.g., a liquid) on passing through an exit orifice of the pressure chamber which holds the second fluid. On leaving the chamber the flow undergoes a large pressure difference between the first fluid (e.g., a liquid) and the second fluid (e.g., a gas), which in turn produces a highly curved zone on the first fluid (e.g., liquid) surface near the exit port of the pressure chamber and in the formation of a cuspidal point from which a steady microjet flows provided the amount of the first fluid (e.g., the liquid) withdrawn through the exit port of the pressure chamber is replenished. Thus, in the same way that a glass lens or a lens of the eye focuses light to a given point, the flow of the gas surrounds and focuses the liquid into a stable microjet. The focusing effect of the surrounding flow of gas creates a stream of liquid which is substantially smaller in diameter than the diameter of the exit orifice of the pressure chamber. This allows liquid to flow out of the pressure chamber orifice without touching the orifice, providing advantages including (1) clogging of the exit orifice is virtually eliminated, (2) contamination of flow due to contact with substances (e.g. bacteria) on the orifice opening is virtually eliminated, and (3) the diameter of the stream and the resulting particles are smaller than the diameter of the exit orifice of the chamber. This is particularly desirable because it is difficult to precisely engineer holes which are very small in diameter. Further, in the absence of the focusing effect (and formation a stable microjet) flow of liquid out of an opening will result in particles which have about twice the diameter of the exit opening. An additional advantage is that the particles are not prone to agglomeration following exit from the chamber.

Specific embodiments of aerosol creation devices are now described.

EMBODIMENT OF FIG. 1

A first embodiment of the invention where the supply means is a cylindrical feeding needle supplying liquid into a pressurized chamber of gas is described below with reference to FIG. 1.

Figure 1:
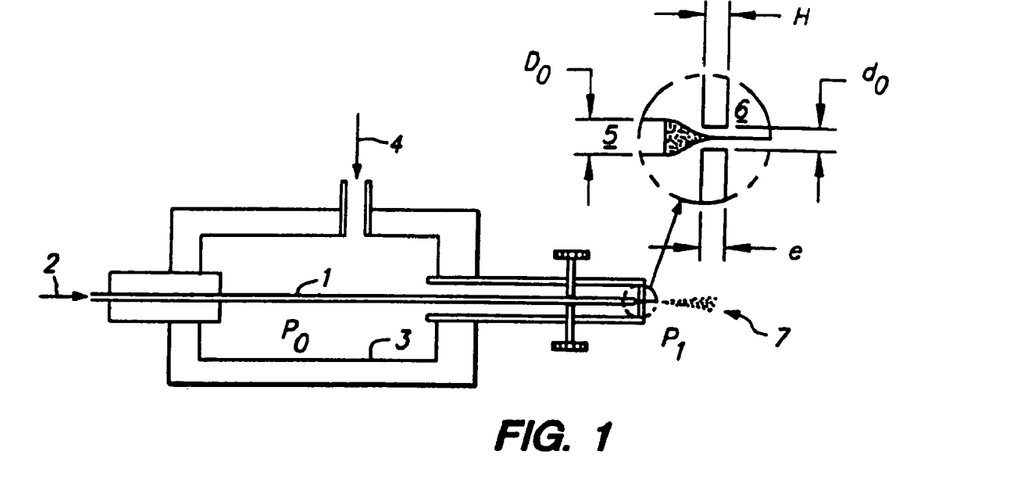
FIG. 1 is a schematic view showing the basic components of one embodiment of the invention with a cylindrical feeding needle as a source of formulation.

The components of the embodiment of FIG. 1 are as follows:
1. Feeding needle—also referred to generally as a fluid source and a tube.
2. End of the feeding needle used to insert the liquid to be atomized.
3. Pressure chamber.
4. Orifice used as gas inlet.
5. End of the feeding needle used to evacuate the liquid to be atomized.
6. Orifice through which withdrawal takes place.
7. Atomizate (spray)—also referred to as aerosol.

$D_0$=diameter of the feeding needle; $d_0$=diameter of the orifice through which the microjet is passed; e=axial length of the orifice through which withdrawal takes place; H=distance from the feeding needle to the microjet outlet; $P_0$=pressure inside the chamber; $P_\alpha$=atmospheric pressure.

An aerosolized drug delivery device of the invention may be any size but is preferably designed to be a hand-held, portable, self-contained device weighing less than 1 kilogram. Although the device can be configured in a variety of designs, the different designs will all include the essential components shown in FIG. 1 or components which perform an equivalent function and obtain the desired results. Specifically, a drug delivery device of the invention will be comprised of at least one source of formulation (e.g., a feeding needle with an opening 2) into which a liquid flowable formulation can be fed and an exit opening 5 from which the formulation can be expelled. The feeding needle 1, or at least its exit opening 5, is encompassed by a pressure chamber 3. The chamber 3 has inlet opening 4 which is used to feed gas into the chamber 3 and an exit opening 6 through which gas from the pressure chamber and liquid formulation from the feeding needle 3 are expelled creating an aerosol.

In FIG. 1, the feeding needle and pressure chamber are configured to obtain a desired result of producing an aerosol wherein the particles are small and uniform in size. Preferably the particles have a size which is in a range of 0.1 to 10 microns, more preferably 1 to 5 microns. Particles of less than 1 micron in diameter can be produced via the present invention. However, particles below 1 micron may be too small for inhalation as the particles may not settle in the lung during a normal breath hold and as such would be exhaled. The particles of any given aerosol all have about the same diameter with a relative standard deviation of 10% to 30% or more preferably 3% to 20%. Stating that particles of the aerosol have a particle diameter in a range of 1 to 5 microns does not mean that different particles will have different diameters and that some will have a diameter of 1 micron while others of 5 microns. The particles in a given aerosol will all (preferably about 90% or more) have the same diameter ±3% to ±30%. For example, the particles of a given aerosol will have a diameter of 2 microns ±3% to ±10%.

Such a monodisperse aerosol is created using the components and configuration as described above. However, other components and configurations will occur to those skilled in the art. The object of each design will be to supply formulation so that it creates a stable capillary microjet which is accelerated and stabilized by tangential viscous stress exerted by the gas on the liquid surface. The stable microjet created by the gas leaves the area of the pressurized gas (e.g., leaves the pressure chamber and exits the pressure chamber orifice) and splits into particles which have the desired size and uniformity.

The aerosol created is a monodisperse aerosol meaning that the size of the particles produced are relatively uniform in size. The relative standard deviation in particle size is in the range of from about 10% to about 30%, preferably 3% to 10% and most preferably 3% or less. The size of aerosolized particles useful for inhalation is a diameter in the range of from about 0.1 micron to about 10 microns, more preferably about 1 micron to about 3 microns.

For purposes of simplicity the remainder of the detailed description of the operation of the device of FIG. 1 will refer to the first fluid as liquid and the second fluid as gas. The parameter window used (i.e. the set of special values for the liquid properties, flow-rate used, feeding needle diameter, orifice diameter, pressure ratio, etc.) should be large enough to be compatible with virtually any liquid (dynamic viscosities in the range from $10^{-4}$ to 1 kg m$^{-1}$s$^{-1}$); in this way, the capillary microjet that emerges from the end of the feeding needle is absolutely stable and perturbations produced by breakage of the jet cannot travel upstream. Downstream, the microjet splits into evenly shaped drops simply by effect of capillary instability (see, for example, Rayleigh, "On the instability of jets", Proc. London Math. Soc., 4–13, 1878), similar in a manner to a laminar capillary jet falling from a half-open tap.

When the stationary, steady interface is created, the capillary jet that emerges from the end of the drop at the outlet of the feeding point is concentrically withdrawn into the nozzle. After the jet emerges from the drop, the liquid is accelerated by tangential sweeping forces exerted by the gas stream flowing on its surface, which gradually decreases the jet cross-section. Stated differently the gas flow acts as a lens and focuses and stabilizes the microjet as it moves toward and into the exit orifice of the pressure chamber.

The forces exerted by the second fluid (e.g., a gas) flow on the first fluid (e.g., a liquid) surface should be steady enough to prevent irregular surface oscillations. Therefore, any turbulence in the gas motion should be avoided; even if the gas velocity is high, the characteristic size of the orifice should ensure that the gas motion is laminar (similar to the boundary layers formed on the jet and on the inner surface of the nozzle or hole).

Stable Capillary Microjet

Figure 4:
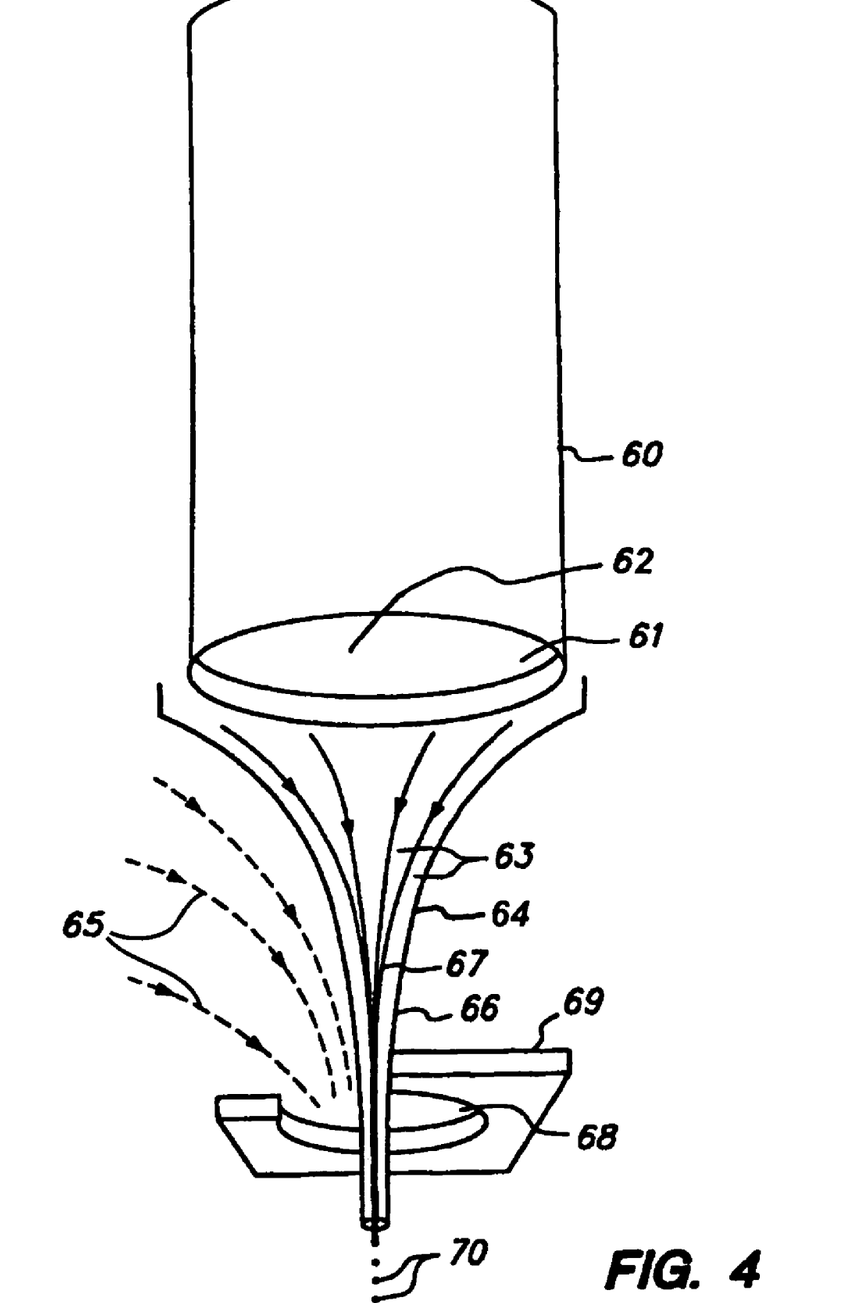
FIG. 4 is a schematic view of a stable capillary microjet being formed and flowing through an exit opening to thereafter form a monodisperse aerosol.

FIG. 4 illustrates the interaction of a liquid and a gas to form atomizate using the method of the invention. The feeding needle 60 has a circular exit opening 61 with an internal radius $R_0$ which feeds a liquid 62 out of the end, forming a drop with a radius in the range of $R_0$ to $R_0$ plus the thickness of the wall of the needle. The exiting liquid forms an infinite amount of liquid streamlines 63 that interact with the surrounding gas to form a stable cusp at the interface 64 of the two fluids. The surrounding gas also forms an infinite number of gas streamlines 65, which interact with the exiting liquid to create a virtual focusing funnel 66. The exiting liquid is focused by the focusing funnel 66 resulting in a stable capillary microjet 67, which remains stable until it exits the opening 68 of the pressure chamber 69. After exiting the pressure chamber, the microjet begins to break-up, forming monodispersed particles 70.

The gas flow, which affects the liquid withdrawal and its subsequent acceleration after the jet is formed, should be very rapid but also uniform in order to avoid perturbing the fragile capillary interface (the surface of the drop that emerges from the jet).

Liquid flows out of the end of a capillary tube and forms a small liquid drop at the end. The tube has an internal radius $R_o$. The drop has a radius in a range of from $R_o$ to $R_o$ plus the structural thickness of the tube as the drop exits the tube, and thereafter the drop narrows in circumference to a much smaller circumference as is shown in the expanded view of the tube (i.e. feeding needle) 5 as shown in FIGS. 1 and 4.

As illustrated in FIG. 4, the exit opening 61 of the capillary tube 60 is positioned close to an exit opening 68 in a planar surface of a pressure chamber 69. The exit opening 68 has a minimum diameter D and is in a planar member with a thickness L. The diameter D is referred to as a minimum diameter because the opening may have a conical configuration with the narrower end of the cone positioned closer to the source of liquid flow. Thus, the exit opening may be a funnel-shaped nozzle although other opening configurations are also possible, e.g. an hour glass configuration. Gas in the pressure chamber continuously flows out of the exit opening. The flow of the gas causes the liquid drop expelled from the tube to decrease in circumference as the liquid moves away from the end of the tube in a direction toward the exit opening of the pressure chamber.

In actual use, it can be understood that the opening shape which provokes maximum gas acceleration (and consequently the most stable cusp and microjet with a given set of parameters) is a conically shaped opening in the pressure chamber. The conical opening is positioned with its narrower end toward the source of liquid flow.

The distance between the end 61 of the tube 60 and the beginning of the exit opening 68 is H. At this point it is noted that $R_o$, D, H and L are all preferably on the order of 
hundreds of microns. For example, $R_o=400$ μm, $D=150$ μm, $H=1$ mm, $L=300$ μm. However, each could be 1/100 to 100× these sizes.

The end of the liquid stream develops a cusp-like shape at a critical distance from the exit opening 68 in the pressure chamber 69 when the applied pressure drop $\Delta P_g$ across the exit opening 68 overcomes the liquid-gas surface tension stresses $\gamma/R^*$ appearing at the point of maximum curvature—e.g. $1/R^*$ from the exit opening.

A steady state is then established if the liquid flow rate Q ejected from the drop cusp is steadily supplied from the capillary tube. This is the stable capillary cusp which is an essential characteristic of the invention needed to form the stable microjet. More particularly, a steady, thin liquid jet with a typical diameter $d_j$ is smoothly emitted from the stable cusp-like drop shape and this thin liquid jet extends over a distance in the range of microns to millimeters. The length of the stable microjet will vary from very short (e.g. 1 micron) to very long (e.g. 50 mm) with the length depending on the (1) flow-rate of the liquid and (2) the Reynolds number of the gas stream flowing out of the exit opening of the pressure chamber. The liquid jet is the stable capillary microjet obtained when supercritical flow is reached. This jet demonstrates a robust behavior provided that the pressure drop $\Delta P_g$ applied to the gas is sufficiently large compared to the maximum surface tension stress (on the order of $\gamma/d_j$) that act at the liquid-gas interface. The jet has a slightly parabolic axial velocity profile which is, in large part, responsible for the stability of the microjet. The stable microjet is formed without the need for other forces, i.e. without adding force such as electrical forces on a charged fluid. However, for some applications it is preferable to add charge to particles, e.g. to cause the particles to adhere to a given surface. The shaping of liquid exiting the capillary tube by the gas flow forming a focusing funnel creates a cusp-like meniscus resulting in the stable microjet. This is a fundamental characteristic of the invention.

The fluid stream flowing from the tube has substantially more density and develops substantially more inertia as compared to the gas, which has lower viscosity than the liquid. These characteristics contribute to the formation of the stable capillary jet. The stable capillary microjet is maintained stably for a significant distance in the direction of flow away from the exit from the tube. The liquid is, at this point, undergoing "supercritical flow." The microjet eventually destabilizes due to the effect of surface tension forces. Destabilization results from small natural perturbations moving downstream, with the fastest growing perturbations being those which govern the break up of the microjet, eventually creating a uniform sized monodisperse aerosol 70 as shown in FIG. 4.

The microjet, even as it initially destabilizes, passes out of the exit orifice of the pressure chamber without touching the peripheral surface of the exit opening. This provides an important advantage of the invention which is that the exit opening 68 (which could be referred to as a nozzle) will not clog from residue and/or deposits of the liquid. Clogging is a major problem with very small nozzles and is generally dealt with by cleaning or replacing the nozzle. When fluid contacts the surfaces of a nozzle opening some fluid will remain in contact with the nozzle when the flow of fluid is shut off. The liquid remaining on the nozzle surface evaporates leaving a residue. After many uses over time the residue builds up and clogging takes place. The present invention substantially reduces or eliminates this clogging problem.

Mathematics of a Stable Microjet

Cylindrical coordinates (r,z) are chosen for making a mathematical analysis of a stable microjet, i.e. liquid undergoing "supercritical flow." The cusp-like meniscus formed by the liquid coming out of the tube is pulled toward the exit of the pressure chamber by a pressure gradient created by the flow of gas.

The cusp-like meniscus formed at the tube's mouth is pulled towards the hole by the pressure gradient created by the gas stream. From the cusp of this meniscus, a steady liquid thread with the shape of radius r=ξ is withdrawn through the hole by the action of both the suction effect due to $\Delta P_g$, and the tangential viscous stresses $\tau_s$ exerted by the gas on the jet's surface in the axial direction. The averaged momentum equation for this $$\frac{d}{d_z}\left[P_1 + \frac{\rho_1 Q^2}{2\pi^2\xi^4}\right] = \frac{2\tau_s}{\xi}, \tag{1}$$

configuration may be written:

where Q is the liquid flow rate upon exiting the feeding tube, $P_1$ is the liquid pressure, and $\rho_1$ is the liquid density, assuming that the viscous extensional term is negligible compared to the kinetic energy term, as will be subsequently justified. In addition, liquid evaporation effects are neglected. The liquid pressure $P_1$ is given by the capillary equation.

$$P_1=P_g/\gamma/\xi \tag{2}$$

where γ is the liquid-gas surface tension. As shown in the Examples, the pressure drop $\Delta P_g$ is sufficiently large as compared to the surface tension stress γ/ξ to justify neglecting the latter in the analysis. This scenario holds for the whole range of flow rates in which the microjet is absolutely stable. In fact, it will be shown that, for a given pressure drop $\Delta P_g$, the minimum liquid flow rate that can be sprayed in steady jet conditions is achieved when the surface tension stress γ/ξ is of the order of the kinetic energy of the liquid $\rho_1 Q^2/(2\pi^2\xi^4)$, since the surface tension acts like a "resistance" to the motion (it appears as a negative term in the right-hand side term of Eq. (1)). Thus, $$Q_{\min} - \left(\frac{\gamma d_j^3}{\rho_1}\right)^{0/00} \tag{3}$$

For sufficiently large flow rates Q compared to $Q_{min}$, the simplified averaged momentum equation in the axial direction can be expressed as $$\frac{d}{d_z}\left(\frac{\rho_1 Q^2}{2\pi^2\xi^4}\right) = \frac{dP_g}{d_z} + \frac{2\tau_s}{\xi}, \tag{4}$$

where one can identify the two driving forces for the liquid flow on the right-hand side. This equation can be integrated provided the following simplification is made: if one uses a thin plate with thickness L of the order or smaller than the hole's diameter D (which minimizes downstream perturbations in the gas flow), the pressure gradient up to the hole exit is on the average much larger than the viscous shear term $2\tau_S/\xi$ owning to the surface stress. On the other hand, the axial viscous term is of the order $O[\mu^2 Q/D^2 d_j^2]$, since the hole diameter D is actually the characteristic distance associated with the gas flow at the hole's entrance in both the radial and axial directions. This term is very small compared to the pressure gradient in real situations, provided that $\Delta P_g \gg \mu^2/D^2 \rho_1$ (which holds, e.g., for liquids with viscosities as large as 100 cpoises, using hole diameters and pressure drops as small as D~10 μm and $\Delta P_g \geqq 100$ mbar). The neglect of all viscous terms in Eq. (4) is then justified. Notice that in this limit on the liquid flow is quasi-isentropic in the average (the liquid almost follows Bernoulli equation) as opposed to most micrometric extensional flows. Thus, integrating (4) from the stagnation regions of both fluids up to the exit, one obtains a simple and universal expression for the jet diameter at the hole exit:

$$d_j = \left(\frac{8\rho_1}{\pi^2 \Delta P_g}\right)^{1/4} Q^{0/00}, \quad (5)$$

which for a given pressure drop $\Delta P_g$ is independent of geometrical parameters (hole and tube diameters, tube-hole distance, etc.), liquid and gas viscosities, and liquid-gas surface tension. This diameter remains almost constant up to the breakup point since the gas pressure after the exit remains constant.

Monodisperse Particles

Above the stable microjet undergoing "supercritical flow" is described and it can be seen how this aspect of the invention can be made use of in a variety of industrial applications—particularly where the flow of liquid through small holes creates a clogging problem. An equally important aspect of the invention is obtained after the microjet leaves the pressure chamber.

When the microjet exits the pressure chamber the liquid pressure $P_1$ becomes (like the gas pressure $P_g$) almost constant in the axial direction, and the jet diameter remains almost constant up to the point where it breaks up by capillary instability. Defining a Weber number We= $(\rho_g v_g^2 d_j)/\gamma \cong 2\Delta P_g d_j/\gamma$ (where $v_g$ is the gas velocity measured at the orifice), below a certain experimental value $We_c \sim 40$ the breakup mode is axisymmetric and the resulting droplet stream is characterized by its monodispersity provided that the fluctuations of the gas flow do not contribute to droplet coalescence (these fluctuations occur when the gas stream reaches a fully developed turbulent profile around the liquid jet breakup region). Above this $We_c$ value, sinuous nonaxisymmetric disturbances, coupled to the axisymmetric ones, become apparent. For larger We numbers, the nonlinear growth rate of the sinuous disturbances seems to overcome that of the axisymmetric disturbances. The resulting spray shows significant polydispersity in this case. Thus, it can be seen that by controlling parameters to keep the resulting Weber number to 40 or less, allows the particles formed to be all substantially the same size. The size variation is about ±3% to ±30% and move preferably ±3% to ±10%. These particles can have a desired size e.g. 0.1 microns to 50 microns.

The shed vorticity influences the breakup of the jet and thus the formation of the particles. Upstream from the hole exit, in the accelerating region, the gas stream is laminar. Typical values of the Reynolds number range from 500 to 6000 if a velocity of the order of the speed of sound is taken as characteristic of the velocity of the gas. Downstream from the hole exit, the cylindrical mixing layer between the gas stream and the stagnant gas becomes unstable by the classical Kelvin-Helmholtz instability. The growth rate of the thickness of this layer depends on the Reynolds number of the flow and ring vortices are formed at a frequency of the order of $v_g/D$, where D is the hole diameter. Typical values of $v_g$ and D as those found in our experimental technique lead to frequencies or the order of MHz which are comparable to the frequency of drop production (of order of $t_b^{-1}$).

Given the liquid flow rate and the hole diameter, a resonance frequency which depends on the gas velocity (or pressure difference driving the gas stream) can be adjusted (tuned) in such a way that vortices act as a forcing system to excite perturbations of a determined wavelength on the jet surface. Experimental results obtained clearly illustrates the different degree of coupling between the two gas-liquid coaxial jets. In one set of experimental results the particle sizes are shown to have a particle size of about 5.7 microns with a standard deviation of 12%. This results when the velocity of the gas has been properly tuned to minimize the dispersion in the size of droplets resulting from the jet breakup. In this case, the flow rate of the liquid jet and its diameter are 0.08 μl s⁻¹ and 3 m, respectively. Data have been collected using a MASTERSIZER from MALVERN Instruments. As the degree of coupling decreases, perturbations at the jet surface of different wavelengths become excited and, as it can be observed from the size distributions, the dispersion of the spray increases.

It is highly desirable in a number of different industrial applications to have particles which are uniform in size or to create aerosols of liquid particles which are uniform in size. For example, particles of a liquid formation containing a pharmaceutically active drug could be created and designed to have a diameter of about 2 microns ±3%. These particles could be inhaled into the lungs of a patient for intrapulmonary drug delivery. Moreover, particle size can be adjusted to target a particular area of the respiratory tract.

The gas flow should be laminar in order to avoid a turbulent regime—turbulent fluctuations in the gas flow which have a high frequency and would perturb the liquid-gas interface. The Reynolds numbers reached at the orifice are $$Re = \frac{v_g d_0}{v_g} - 4000$$

where $v_g$ is the kinematic viscosity of the gas. Even though this number is quite high, there are large pressure gradients downstream (a highly convergent geometry), so that a turbulent regime is very unlikely to develop.

The essential difference from existing pneumatic atomizers (which possess large Weber numbers) and the present invention is that the aim of the present invention is not to rupture the liquid-gas interface but the opposite, i.e. to increase the stability of the interface until a capillary jet is obtained. The jet, which will be very thin provided the pressure drop resulting from withdrawal is high enough, splits into drops the sizes of which are much more uniform than those resulting from disorderly breakage of the liquid-gas interface in existing pneumatic atomizers.

The proposed atomization system obviously requires delivery of the liquid to be atomized and the gas to be used in the resulting spray. Both should be fed at a rate ensuring that the system lies within the stable parameter window. Multiplexing is effective when the flow-rates needed exceed those on an individual cell. More specifically, a plurality of feeding sources or feeding needles may be used to increase the rate at which aerosols are created. The flow-rates used should also ensure the mass ratio between the flows is compatible with the specifications of each application.

The gas and liquid can be dispensed by any type of continuous delivery system (e.g. a compressor or a pressurized tank the former and a volumetric pump or a pressurized bottle the latter). If multiplexing is needed, the liquid flow-rate should be as uniform as possible among cells; this may entail propulsion through several capillary needles, porous media or any other medium capable of distributing a uniform flow among different feeding points.

Each individual atomization device should consist of a feeding point (a capillary needle, a point with an open microchannel, a microprotuberance on a continuous edge, etc.) 0.002–2 mm (but, preferentially 0.01–0.4 mm) in diameter, where the drop emerging from the microjet can be anchored, and a small orifice 0.002–2 mm (preferentially 0.01–0.25 mm) in diameter facing the drop and separated 0.01–2 mm (preferentially 0.2–0.5 mm) from the feeding point. The orifice communicates the withdrawal gas around the drop, at an increased pressure, with the zone where the atomizate is produced, at a decreased pressure. The atomizer can be made from a variety of materials (metal, polymers, ceramics, glass).

FIG. 1 depicts a tested prototype where the liquid to be atomized is inserted through one end of the system 2 and the propelling gas in introduced via the special inlet 4 in the pressure chamber 3. The prototype was tested at gas feeding rates from 100 to 2000 mBar above the atmospheric pressure $P_a$ at which the atomized liquid was discharged. The whole enclosure around the feeding needle 1 was at a pressure $P_0 > P_a$. The liquid feeding pressure, $P_1$, should always be slightly higher than the gas propelling pressure, $P_o$. Depending on the pressure drop in the needle and the liquid feeding system, the pressure difference $(P_1 - P_0 > 0)$ and the flow-rate of the liquid to be atomized, Q, are linearly related provided the flow is laminar—which is indeed the case with this prototype. The critical dimensions are the distance from the needle to the plate (H), the needle diameter ($D_0$), the diameter of the orifice through which the microjet 6 is discharged ($d_0$) and the axial length, e, of the orifice (i.e. the thickness of the plate where the orifice is made). In this prototype, H was varied from 0.3 to 0.7 mm on constancy of the distances ($D_0$=0.45 mm, $d_0$–0.2 mm) and e–0.5 mm. The quality of the resulting spray 7 did not vary appreciably with changes in H provided the operating regime (i.e. stationary drop and microjet) was maintained. However, the system stability suffered at the longer H distances (about 0.7 mm). The other atomizer dimensions had no effect on the spray or the prototype functioning provided the zone around the needle (its diameter) was large enough relative to the feeding needle.

Weber Number

Adjusting parameters to obtain a stable capillary microjet and control its breakup into monodisperse particle is governed by the Weber number and the liquid-to-gas velocity ratio or a which equal $V_1/V_g$. The Weber number or "We" is defined by the following equation:

$$We = \frac{\rho_g v_g^2 d}{\gamma}$$

wherein $\rho_g$ is the density of the gas, d is the diameter of the stable microjet, $\gamma$ is the liquid-gas surface tension, and $V^{g2}$ is the velocity of the gas squared.

When carrying out the invention the parameters should be adjusted so that the Weber number is greater than 1 in order to produce a stable capillary microjet. However, to obtain a particle dispersion which is monodisperse (i.e. each particle has the same size ±3 to ±30%) the parameters should be adjusted so that the Weber number is less than 40. The monodisperse aerosol is obtained with a Weber number in a range of about 1 to about 40 when the breaking time is sufficiently small to avoid non-symmetric perturbations $(1 \leq We \leq 40)$.

Ohnesorge Number

A measure of the relative importance of viscosity on the jet breakup can be estimated from the Ohnesorge number defined as the ratio between two characteristic times: the viscous time $t_v$ and the breaking time $t_b$. The breaking time $t_b$ is given by [see Rayleigh (1878)]

$$t_b - \left(\frac{\rho_1 d^2}{\gamma}\right)^{0/00}. \tag{2}$$

Perturbations on the jet surface are propagated inside by viscous diffusion in times $t_v$ of the order of $$t_v\_\rho_1 d^2\_\mu_1, \tag{3}$$

where $\mu_1$ is the viscosity of the liquid. Then, the Ohnesorge number, Oh, results $$Oh = \frac{\mu_1}{(\rho_1 \gamma d)^{0/00}}. \tag{4}$$

If this ratio is much smaller than unity viscosity plays no essential role in the phenomenon under consideration. Since the maximum value of the Ohnesorge number in actual experiments conducted is as low as $3.7 \times 10^{-2}$, viscosity plays no essential role during the process of jet breakup.

EMBODIMENT OF FIG. 2

Figure 2:
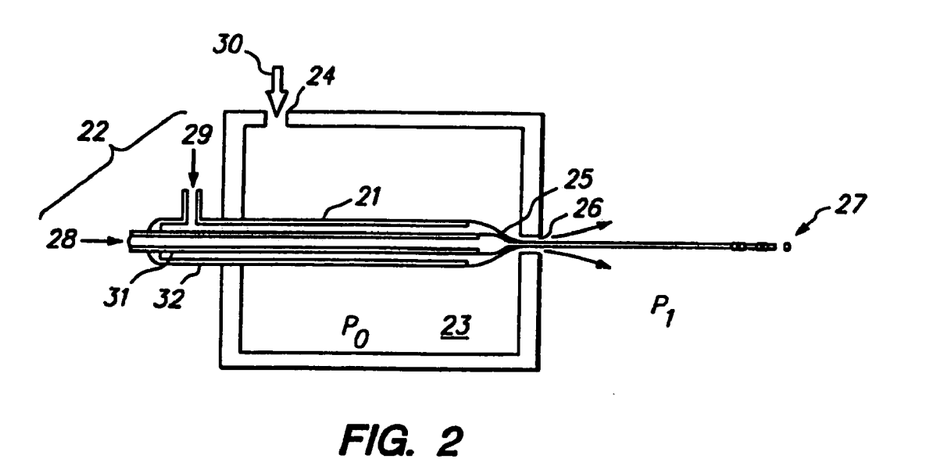
FIG. 2 is a schematic view of another embodiment of the invention with two concentric tubes as a source of formulation.

A variety of configurations of components and types of fluids will become apparent to those skilled in the art upon reading this disclosure. These configurations and fluids are encompassed by the present invention provided they can produce a stable capillary microjet of a first fluid from a source to an exit port of a pressure chamber containing a second fluid. The stable microjet is formed by the first fluid flowing from the feeding source to the exit port of the pressure chamber being accelerated and stabilized by tangential viscous stress exerted by the second fluid in the pressure chamber on the surface of the first fluid forming the microjet. The second fluid forms a focusing funnel when a variety of parameters are correctly tuned or adjusted. For example, the speed, pressure, viscosity and miscibility of the first and second fluids are chosen to obtain the desired results 
of a stable microjet of the first fluid focused into the center of a funnel formed with the second fluid. These results are also obtained by adjusting or tuning physical parameters of the device, including the size of the opening from which the first fluid flows, the size of the opening from which both fluids exit, and the distance between these two openings.

The embodiment of FIG. 1 can, itself, be arranged in a variety of configurations. Further, as indicated above, the embodiment may include a plurality of feeding needles. A plurality of feeding needles may be configured concentrically in a single construct, as shown in FIG. 2.

The components of the embodiment of FIG. 2 are as follows:

21. Feeding needle—tube or source of fluid.
22. End of the feeding needle used to insert the liquids to be atomized.
23. Pressure chamber.
Orifice used as gas inlet.
End of the feeding needle used to evacuate the liquid to be atomized.
26. Orifice through which withdrawal takes place.
27. Atomizate (spray) or aerosol.
28. First liquid to be atomized (inner core of particle).
29. Second liquid to be atomized (outer coating of particle).
30. Gas for creation of microjet.
31. Internal tube of feeding needle.
32. External tube of feeding needle.

D=diameter of the feeding needle; d=diameter of the orifice through which the microjet is passed; e=axial length of the orifice through which withdrawal takes place; H=distance from the feeding needle to the microjet outlet; $\gamma$=surface tension; $P_0$=pressure inside the chamber; $P_\alpha$=atmospheric pressure.

The embodiment of FIG. 2 is preferably used when attempting to form a spherical particle of one substance coated by another substance. The device of FIG. 2 is comprised of the same basic component as per the device of FIG. 1 and further includes a second feeding source 32 which is positioned concentrically around the first cylindrical feeding source 31. The second feeding source may be surrounded by one or more additional feeding sources with each concentrically positioned around the preceding source. The outer coating may be used for a variety of purposes, including: coating particles to prevent small particles from sticking together; to obtain a sustained release effect of the active compound (e.g. a pharmaceutically active drug) inside, and/or to mask flavors; and to protect the stability of another compound (e.g. a pharmaceutically active drug) contained therein.

The process is based on the microsuction which the liquid-gas or liquid-liquid interphase undergoes (if both are immiscible), when said interphase approaches a point beginning from which one of the fluids is suctioned off while the combined suction of the two fluids is produced. The interaction causes the fluid physically surrounded by the other to form a capillary microjet which finally breaks into spherical drops. If instead of two fluids (gas-liquid), three or more are used that flow in a concentric manner by injection using concentric tubes, a capillary jet composed of two or more layers of different fluids is formed which, when it breaks, gives rise to the formation of spheres composed of several approximately concentric spherical layers of different fluids. The size of the outer sphere (its thickness) and the size of the inner sphere (its volume) can be precisely adjusted. This can allow the manufacture of coated particles for a variety of end uses. For example the thickness of the coating can be varied in different manufacturing events to obtain coated particles which have gradually decreasing thicknesses to obtain a controlled release effect of the contents, e.g. a pharmaceutically active drug. The coating could merely prevent the particles from degrading, reacting, or sticking together.

The method is based on the breaking of a capillary microjet composed of a nucleus of one liquid or gas and surrounded by another or other liquids and gases which are in a concentric manner injected by a special injection head, in such a way that they form a stable capillary microjet and that they do not mix by diffusion during the time between when the microjet is formed and when it is broken. When the capillary microjet is broken into spherical drops under the proper operating conditions, which will be described in detail below, these drops exhibit a spherical nucleus, the size and eccentricity of which can be controlled.

In the case of spheres containing two materials, the injection head 25 consists of two concentric tubes with an external diameter on the order of one millimeter. Through the internal tube 31 is injected the material that will constitute the nucleus of the microsphere, while between the internal tube 31 and the external tube 32 the coating is injected. The fluid of the external tube 32 joins with the fluid of tube 31 as the fluids exit the feeding needle, and the fluids (normally liquids) thus injected are accelerated by a stream of gas that passes through a small orifice 24 facing the end of the injection tubes. When the drop in pressure across the orifice 24 is sufficient, the liquids form a completely stationary capillary microjet, if the quantities of liquids that are injected are stationary. This microjet does not touch the walls of the orifice, but passes through it wrapped in the stream of gas or funnel formed by gas from the tube 32. Because the funnel of gas focuses the liquid, the size of the exit orifice 26 does not dictate the size of the particles formed.

When the parameters are correctly adjusted, the movement of the liquid is uniform at the exit of the orifice 26 and the viscosity forces are sufficiently small so as not to alter either the flow or the properties of the liquids; for example, if there are biochemical molecular specimens having a certain complexity and fragility, the viscous forces that would appear in association with the flow through a micro-orifice might degrade these substances.

FIG. 2 shows a simplified diagram of the feeding needle 21, which is comprised of the concentric tubes 30, 31 through the internal and external flows of the fluids 28, 29 that are going to compose the microspheres comprised of two immiscible fluids. The difference in pressures $P_0-P_\alpha$ ($P_0>P_\alpha$) through the orifice 26 establishes a flow of gas present in the chamber 23 and which is going to surround the microjet at its exit. The same pressure gradient that moves the gas is the one that moves the microjet in an axial direction through the hole 26, provided that the difference in pressures $P_0-P_\alpha$ is sufficiently great in comparison with the forces of surface tension, which create an adverse gradient in the direction of the movement.

There are two limitations for the minimum sizes of the inside and outside jets that are dependent (a) on the surface tensions $\gamma 1$ of the outside liquid 29 with the gas 30 and $\gamma 2$ of the outside liquid 29 with the inside liquid 28, and (b) on the difference in pressures $\Delta P=P_0-P_\alpha$ through the orifice 26. In the first place, the jump in pressures $\Delta P$ must be sufficiently great so that the adverse effects of the surface tension are minimized. This, however, is attained for very modest pressure increases: for example, for a 10 micron jet of a liquid having a surface tension of 0.05 N/m (tap water), the necessary minimum jump in pressure is in the order of 0.05

(N/m)/0.00001 m=ΔP=50 mBar. But, in addition, the breakage of the microjet must be regular and axilsymmetric, so that the drops will have a uniform size, while the extra pressure ΔP cannot be greater than a certain value that is dependent on the surface tension of the outside liquid with the gas γ1 and on the outside diameter of the microjet. It has been experimentally shown that this difference in pressures cannot be greater than 20 times the surface tension γ1 divided by the outside radius of the microjet.

Therefore, given some inside and outside diameters of the microjet, there is a range of operating pressures between a minimum and a maximum; nonetheless, experimentally the best results are obtained for pressures in the order of two to three times the minimum.

Figure 3A:
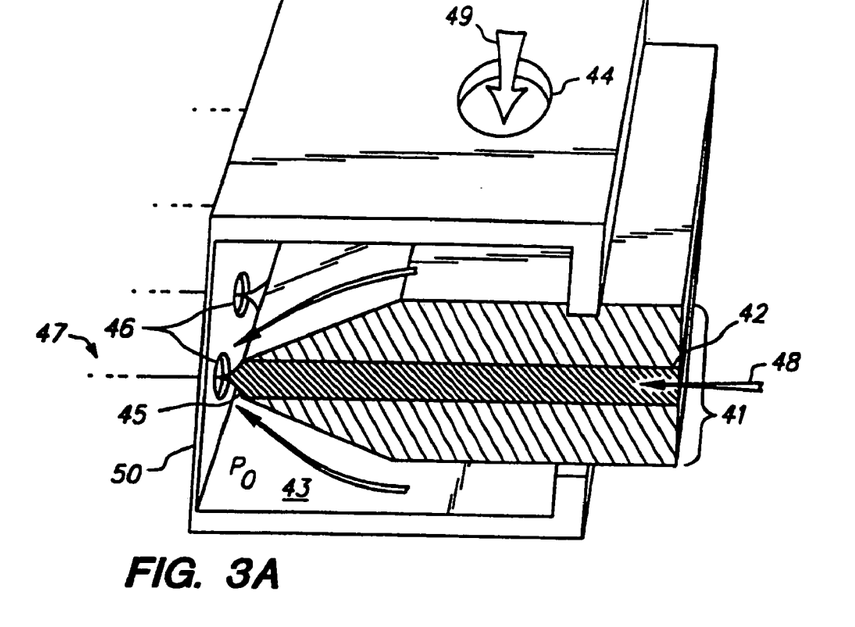
FIG. 3a illustrates a cross-sectional side view of the planar feeding source and the interaction of the fluids.
Figure 3B:
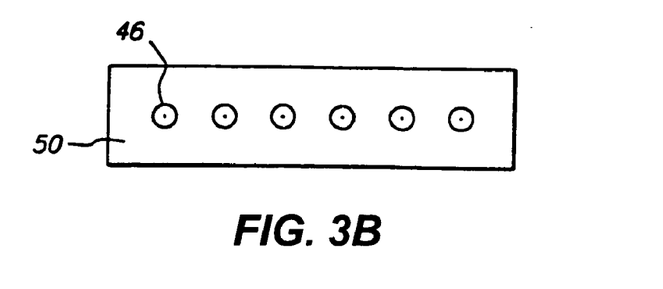
FIG. 3b show a frontal view of the openings in the pressure chamber, with the multiple openings through which the atomizate exits the device.
Figure 3C:
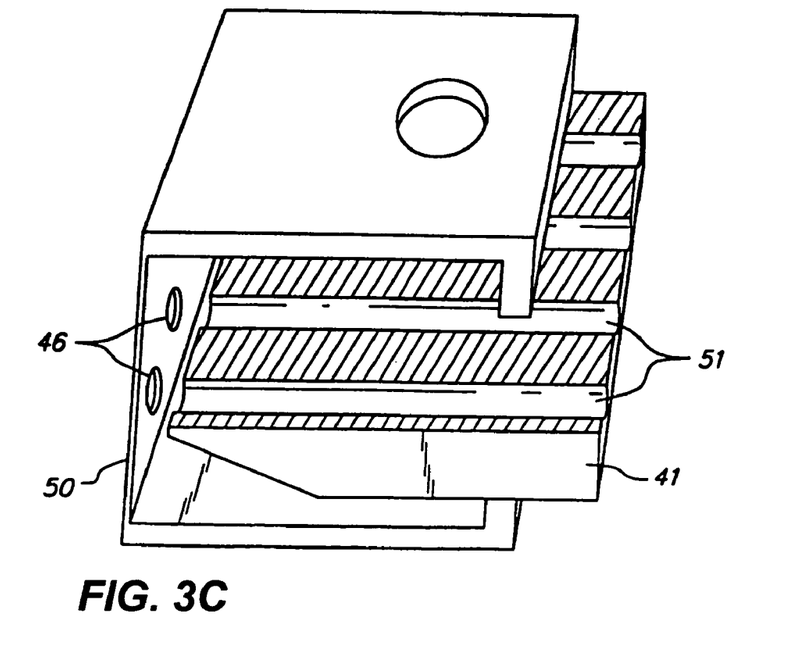
FIG. 3c illustrates the channels that are optionally formed within the planar feeding member. The channels are aligned with the openings in the pressure chamber.

The viscosity values of the liquids must be such that the liquid with the greater viscosity $\mu_{max}$ verifies, for a diameter d of the jet predicted for this liquid and a difference through the orifice ΔP, the inequality:

$$\mu_{max} \leq \frac{\Delta P d^2 D}{Q}$$

With this, the pressure gradients can overcome the extensional forces of viscous resistance exerted by the liquid when it is suctioned toward the orifice.

Moreover, the liquids must have very similar densities in order to achieve the concentricity of the nucleus of the microsphere, since the relation of velocities between the liquids moves according to the square root of the densities $v1/v2=(\rho 2/\rho 1)^{1/2}$ and both jets, the inside jet and the outside jet, must assume the most symmetrical configuration possible, which does not occur if the liquids have different velocities (FIG. 2). Nonetheless, it has been experimentally demonstrated that, on account of the surface tension γ2 between the two liquids, the nucleus tends to migrate toward the center of the microsphere, within prescribed parameters.

When two liquids and gas are used on the outside, the distance between the planes of the mouths of the concentric tubes can vary, without the characteristics of the jet being substantially altered, provided that the internal tube 31 is not introduced into the external one 32 more than one diameter of the external tube 32 and provided that the internal tube 31 does not project more than two diameters from the external tube 32. The best results are obtained when the internal tube 31 projects from the external one 32 a distance substantially the same as the diameter of the internal tube 31. This same criterion is valid if more than two tubes are used, with the tube that is surrounded (inner tube) projecting beyond the tube that surrounds (outer tube) by a distance substantially the same as the diameter of the first tube.

The distance between the plane of the internal tube 31 (the one that will normally project more) and the plane of the orifice may vary between zero and three outside diameters of the external tube 32, depending on the surface tensions between the liquids and with the gas, and on their viscosity values. Typically, the optimal distance is found experimentally for each particular configuration and each set of liquids used.

The proposed atomizing system obviously requires fluids that are going to be used in the resulting spray to have certain flow parameters. Accordingly, flows for this use must be:

Flows that are suitable so that the system falls within the parametric window of stability. Multiplexing (i.e. several sets of concentric tubes) may be used, if the flows required are greater than those of an individual cell.

Flows that are suitable so that the mass relation of the fluids falls within the specifications of each application. Of course, a greater flow of gas may be supplied externally by any means in specific applications, since this does not interfere with the functioning of the atomizer.

If the flows are varied, the characteristic time of this variation must be less than the hydrodynamic residence times of liquid and gas in the microjet, and less than the inverse of the first natural oscillation frequency of the drop formed at the end of the injection needle.

Therefore, any means for continuous supply of gas (compressors, pressure deposits, etc.) and of liquid (volumetric pumps, pressure bottles) may be used. If multiplexing is desired, the flow of liquid must be as homogeneous as possible between the various cells, which may require impulse through multiple capillary needles, porous media, or any other medium capable of distributing a homogeneous flow among different feeding points.

Each atomizing device will consist of concentric tubes 31, 32 with a diameter ranging between 0.05 and 2 mm, preferably between 0.1 and 0.4 mm, on which the drop from which the microjet emanates can be anchored, and a small orifice (between 0.001 and 2 mm in diameter, preferably between 0.1 and 0.25 mm), facing the drop and separated from the point of feeding by a distance between 0.001 and 2 mm, preferably between 0.2 and 0.5 mm. The orifice puts the suction gas that surrounds the drop, at higher pressure, in touch with the area in which the atomizing is to be attained, at lower pressure.

EMBODIMENT OF FIG. 3

The embodiments of FIGS. 1 and 2 are similar in a number of ways. Both have a feeding piece which is preferably in the form of a feeding needle with a circular exit opening. Further, both have an exit port in the pressure chamber which is positioned directly in front of the flow path of fluid out of the feeding source. Precisely maintaining the alignment of the flow path of the feeding source with the exit port of the pressure chamber can present an engineering challenge particularly when the device includes a number of feeding needles. The embodiment of FIG. 3 is designed to simplify the manner in which components are aligned. The embodiment of FIG. 3 uses a planar feeding piece (which by virtue of the withdrawal effect produced by the pressure difference across a small opening through which fluid is passed) to obtain multiple microjets which are expelled through multiple exit ports of a pressure chamber thereby obtaining multiple aerosol streams. Although a single planar feeding member as shown in FIG. 3 it, of course, is possible to produce a device with a plurality of planar feeding members where each planar feeding member feeds fluid to a linear array of outlet orifices in the surrounding pressure chamber. In addition, the feeding member need not be strictly planar, and may be a curved feeding device comprised of two surfaces that maintain approximately the same spatial distance between the two pieces of the feeding source. Such curved devices may have any level of curvature, e.g. circular, semicircular, elliptical, hemi-elliptical etc.

The components of the embodiment of FIG. 3 are as follows:

41. Feeding piece.

42. End of the feeding piece used to insert the fluid to be atomized.

43. Pressure chamber.

44. Orifice used as gas inlet.

45. End of the feeding needle used to evacuate the liquid to be atomized.
46. Orifices through which withdrawal takes place.
47. Atomizate (spray) or aerosol.
48. first fluid containing material to be atomized.
49. second fluid for creation of microjet.
50. wall of the propulsion chamber facing the edge of the feeding piece.
51. channels for guidance of fluid through feeding piece.

$d_j$=diameter of the microjet formed; $\rho_A$=liquid density of first fluid (48); $92_B$=liquid density of second fluid (49); $v_A$=velocity of the first liquid (48); $v_B$=velocity of the second liquid (49); e=axial length of the orifice through which withdrawal takes place; H=distance from the feeding needle to the microjet outlet; $P_0$=pressure inside the chamber;

$\Delta p_g$=change in pressure of the gas; $P_\alpha$=atmospheric pressure; Q-volumetric flow rate The proposed dispersing device consists of a feeding piece 41 which creates a planar feeding channel through which a where a first fluid 48 flows. The flow is preferably directed through one or more channels of uniform bores that are constructed on the planar surface of the feeding piece 41. A pressure chamber 43 that holds the propelling flow of a second liquid 49, houses the feeding piece 41 and is under a pressure above maintained outside the chamber wall 50. One or more orifices, openings or slots (outlets) 46 made in the wall 52 of the propulsion chamber face the edge of the feeding piece. Preferably, each bore or channel of the feeding piece 41 has its flow path substantially aligned with an outlet 46.

Formation of the microjet and its acceleration are based on the abrupt pressure drop resulting from the steep acceleration undergone by the second fluid 49 on passing through the orifice 46, similarly to the procedure described above for embodiments of FIGS. 1 and 2 when the second fluid 49 is a gas.

When the second fluid 49 is a gas and the first fluid 48 is a liquid, the microthread formed is quite long and the liquid velocity is much smaller than the gas velocity. In fact, the low viscosity of the gas allows the liquid to flow at a much lower velocity; as a result, the microjet is actually produced and accelerated by stress forces normal to the liquid surface, i.e. pressure forces. Hence, one effective approximation to the phenomenon is to assume that the pressure difference established will result in the same kinetic energy per unit volume for both fluids (liquid and gas), provided gas compressibility effects are neglected. The diameter $d_j$ of the microjet formed from a liquid density $\rho_1$ that passes at a volumetric flow-rate Q through an orifice across which a pressure difference $\Delta P_g$ exists will be given by $$d_j - \left(\frac{8\rho_1}{\pi^2 \Delta P_g}\right)^{1/4} Q^{0/00}$$

See Gañàn-Calvo, *Physical Review Letters*, 80:285–288 (1998).

The relation between the diameter of the microjet, $d_j$, and that of the resulting drops, _, depends on the ratio between viscous forces and surface tension forces on the liquid on the one hand, and between dynamic forces and surface tension forces on the gas on the other (i.e. on the Ohnesorge and Weber numbers, respectively) (Hinds (*Aerosol Technology*, John & Sons, 1982), Lefevre (*Atomization and Sprays*, Hemisphere Pub. Corp., 1989) and Bayvel & Orzechowski (*Liquid Atomization*, Taylor & Francis, 1993)). At moderate to low gas velocities and low viscosities the relation is roughly identical with that for capillarity instability developed by Rayleigh:

$$\_ = 1.89 d_j$$

Because the liquid microjet is very long, at high liquid flow-rates the theoretical rupture point lies in the turbulent zone created by the gas jet, so turbulent fluctuations in the gas destabilize or rupture the liquid microjet in a more or less uneven manner. As a result, the benefits of drop size uniformity are lost.

On the other hand, when the second fluid 49 is a liquid and the first fluid 48 is a gas, the facts that the liquid is much more viscous and that the gas is much less dense virtually equalize the fluid and gas velocities. The gas microthread formed is much shorter; however, because its rupture zone is almost invariably located in a laminar flowing stream, dispersion in the size of the microbubbles formed is almost always small. At a volumetric gas flow-rate $Q_g$ and a liquid overpressure $\Delta P_1$, the diameter of the gas microjet is given by $$d_j - \left(\frac{8\rho_1}{\pi^2 \Delta P_1}\right)^{1/4} Q_g^{1/2}$$

The low liquid velocity and the absence of relative velocities between the liquid and gas lead to the Rayleigh relation between the diameters of the microthread and those of the bubbles (i.e. $d = 1.89 d_j$).

If both fluids 48, 49 are liquid and scarcely viscous, then their relative velocities will be given by $$\frac{v_A}{v_B} = \left(\frac{\rho_B}{\rho_A}\right)^{0/00}$$

The diameter of a microjet of the first liquid at a volumetric flow-rate of A $Q_A$ and $$d_j - \left(\frac{8\rho_A}{\pi^2 \Delta P_B}\right)^{1/4} Q_A^{1/2}$$

an overpressure of $B\Delta P_B$ will be given by

At viscosities such that the velocities of both fluids 48, 49 will rapidly equilibrate in the microjet, the diameter of the microjet of the first liquid will be given by $$d_j - \left(\frac{8\rho_A}{\pi^2 \Delta P_B}\right)^{1/4} Q_A^{1/2}$$

The proposed atomization system obviously requires delivery of the fluids 48, 49 to be used in the dispersion process at appropriate flow-rates. Thus:

(1) Both flow-rates should be adjusted for the system so that they lie within the stable parameter window.

(2) The mass ratio between the flows should be compatible with the specifications of each application. Obviously, the gas flow-rate can be increased by using an external means in special applications (e.g. burning, drug inhalation) since this need not interfere with the atomizer operation.

(3) If the flow-rates are altered, the characteristic time for the variation should be shorter than the hydrodynamic residence times for the liquid and gas in the microjet, and smaller than the reciprocal of the first natural oscillation frequency of the drop formed at the end of the feeding piece.

(4) Therefore, the gas and liquid can be dispensed by any type of continuous delivery system (e.g. a compressor or a pressurized tank the former and a volumetric pump or a pressurized bottle the latter).

(5) The atomizer can be made from a variety of materials (metal, plastic, ceramics, glass).

Drug Delivery Devices

The various embodiments of components for creating aerosols described above can be used in devices for the delivery of an aerosol to a patient. The device is preferably a hand-held, self-contained device which a patient can easily carry about and use for the administration of drugs.

In one embodiment the pressurized canister of a device as disclosed in U.S. Pat. No. 5,364,838 or 5,404,871 is replaced with an aerosol generating device of the type shown here in any of FIG. 1, 2 or 3. The device preferably includes a means for measuring a patient's respiratory flow rate and respiratory volume. The aerosol may be generated when the patient manually actuates release of aerosol. However, the device preferably operates as the device in the U.S. Pat. No. 5,364,838 and is actuated automatically in response to a measured inspiratory flow rate and inspiratory volume. This makes it possible to repeatedly deliver aerosol to a patient at the same point in the respiratory cycle thereby improving repeatability of dosing.

In another embodiment the disposable containers and porous membranes of the device disclosed in U.S. Pat. No. 5,544,646 is replaced with an aerosol generating device of the type shown here in FIG. 1, 2 or 3. In such an embodiment the aerosol generating device is likely to include a plurality of sources of liquid drug formulation (e.g. a plurality of feeding needles) so that a sufficient amount of formulation can be aerosolized in a sufficiently short period of time that the patient can, in a single inhalation, inhale all of the aerosol needed for a dose of the drug being delivered. An aerosol generating device of the type shown in FIG. 3 is generally easier to manufacture and as such is preferred in this embodiment.

In the two embodiments described above it is preferable to create an aerosol with particles having a particle diameter in the range of about 1 to about 3 microns. This allows the particles to penetrate into the smallest channels of the lungs. However, such particles are not so small that they will not settle on the surface of these channels when inhaled—failure to settle would cause the particles to be exhaled as with particles of smoke.

In yet another embodiment the source of aerosol of a device as disclosed in U.S. Pat. No. 4,484,577 is replaced with an aerosol generating device of the type described here and shown in FIG. 1, 2 or 3. The device of U.S. Pat. No. 4,484,577 includes a large container into which the aerosol is dispersed. The aerosol then "hangs" in the air in the large container until it is inhaled by the patient. Using an aerosol generation device of the invention the aerosol particles can be made very small, e.g. about 1 micron or less. Particles of this size will be suspended in air in the container until inhaled. The patient can then breath normally in and out of the container until all or substantially all particles in the container have deposited themselves on the channels of the lung.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The properties of sixteen different liquids are provided in Table 1

TABLE 1

Liquids used and some of their physical properties at 24.5° C. ($\rho$: kg/m$^3$, $\mu$: cpoise, $\gamma$: N/m). Also given, the symbols used in the plots.

| Liquid | $\rho$ | $\mu$ | $\gamma$ | Symbol |
|---|---|---|---|---|
| Heptane | 684 | 0.38 | 0.021 | ○ |
| Tap Water | 1000 | 1.00 | 0.056 | ◇ |
| Water + glycerol 90/10 v/v | 1026 | 1.39 | 0.069 | △ |
| Water + glycerol 80/20 v/v | 1052 | 1.98 | 0.068 | ▽ |
| Isopropyl alcohol | 755.5 | 2.18 | 0.021 | × |
| Water + glycerol 70/30 v/v | 1078 | 2.76 | 0.067 | 0 |
| Water + glycerol 60/40 v/v | 1104 | 4.37 | 0.067 | ● |
| Water + glycerol 50/50 v/v | 1030 | 6.17 | 0.066 | ○ |
| 1-Octanol | 827 | 7.47 | 0.024 | ◇ |
| Water + glycerol 40/60 v/v | 1156 | 12.3 | 0.065 | △ |
| Water + glycerol 35/65 v/v | 1167 | 15.9 | 0.064 | ▽ |
| Water + glycerol 30/70 v/v | 1182 | 24.3 | 0.064 | × |
| Water + glycerol 25/75 v/v | 1195 | 38.7 | 0.063 | + |
| Propylene glycol | 1026 | 41.8 | 0.036 | ● |

The liquids of Table 1 were forced through a feeding needle of the type shown in FIG. 1. The end 5 of the feeding needle had an internal radius $R_o$. The exit orifice 6 had a diameter D and the wall of the pressure chamber 3 had a thickness of L. Three different devices were tested having the following dimensions: (D=0.15, 0.2, and 0.3 mm; L=0.1, 0.2 and 0.35 mm; $R_o$+0.2, 0.4, and 0.6 mm, respectively), and several distances H from the tube mouth to the orifice ranging from H=0.5 mm to H=1.5 mm have been used. The jet diameter was measured at the hole exit and was plotted as a function of the pressure difference $\Delta P_g$ and flow rate Q respectively. Although this technique allows for jet diameters even below one micron, larger flow rates and diameters have been used in this study to diminish the measuring errors.

In order to collapse all of the data, we define a reference flow rate $Q_o$ and diameter $d_o$ based on the minimal values, from expressions (3) and (5), that can be attained in stable regime for a given $\Delta P_g$:

$$Q_o = \left(\frac{\gamma^4}{\rho_1 \Delta P_g^3}\right)^{0/00}, \quad d_o^* = \frac{\gamma}{\Delta P_g} \quad (6)$$

These definitions provide the advantage of a nondimensional expression for (5), as $$d_j/d_o = (8/\pi^2)^{1/4}(Q/Q_o)^{1/2}, \quad (7)$$

which allows for a check for the validity of neglecting the surface tension term in (4) (i.e., $Q/Q_o$ should be large).

Notice that if the measured $d_j$ follows expression (5), the surface tension cancels out in (7). Also notice that $d_j/d_o \cong We/2$.

Figure 5:
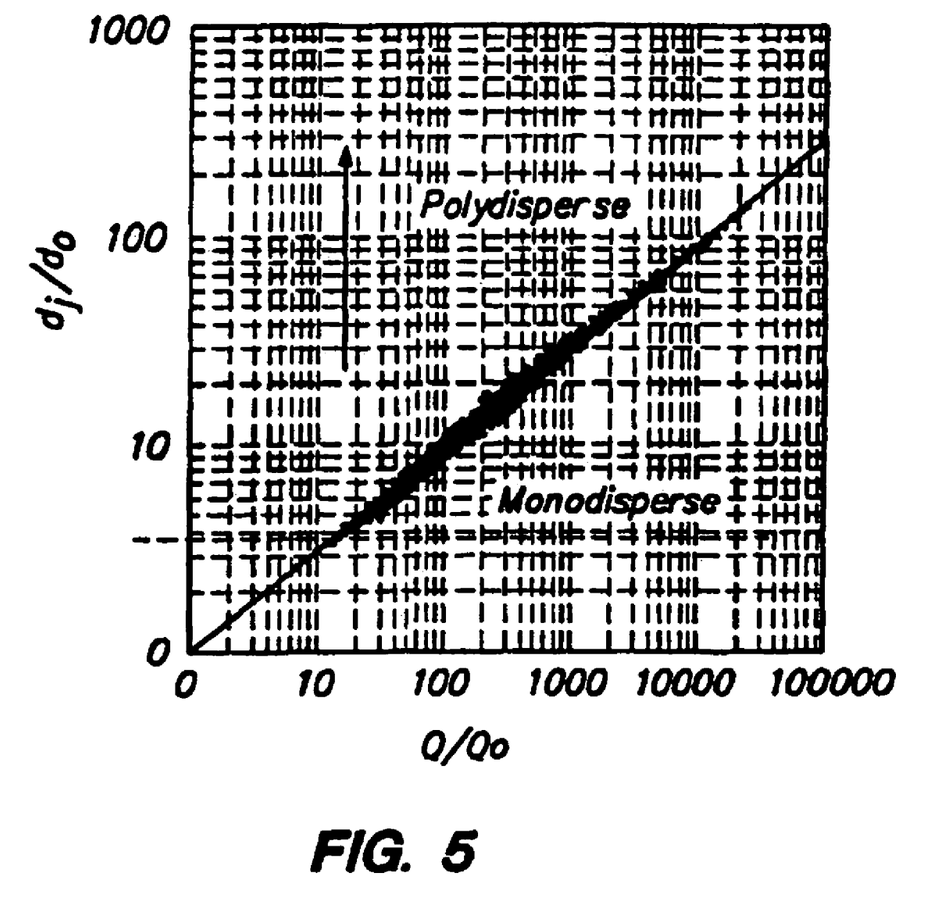
FIG. 5 is a graph of data where 350 measured valves of $d_j/d_o$ versus $Q/Q_o$ are plotted.

350 measured values of $d_j/d_o$ versus $Q/Q_o$ are plotted in FIG. 5. A continuous line represents the theoretical prediction (7), independent of liquid viscosity and surface tension. The use of different hole and tube diameters as well as tube-hole distances does not have any appreciable influence on $d_j$. The collapse of the experimental data and the agreement with the simple theoretical model is excellent. Finally, the experimental values of Q are at least four times large than $Q_o$ (being in most cases several hundreds times larger), which justifies the neglect of the surface tension term in Eq. (4).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. The method of delivering an aerosol to the patient, comprising:
    feeding a pharmaceutically active drug through a cylindrical channel of a feeding source in a manner which causes the liquid to be expelled from an exit opening as a liquid stream wherein the exit opening has a diameter in a range of from about 0.002 mm to about 2 mm;
    forcing a gas through a pressure chamber in a manner which causes the gas to exit the pressure chamber from an exit orifice having a diameter in a range of about 0.002 mm to about 2 mm, the gas exiting downstream of a flow path of the liquid stream expelled from the exit opening of the feeding source;
    wherein the exit opening of the feeding source is separated by a distance of from about 0.002 mm to about 2 mm from the exit opening of the feeding source;
    wherein the liquid stream is accelerated by tangential viscous stress exerted by the gas on the stream and the liquid is focused on the exit orifice of the pressure chamber by the gas.

2. The method of claim 1, wherein the liquid has a viscosity in a range of from about $10^{-4}$ to about 1 kg/m/sec.

3. The method of claim 1, wherein the gas is air.

4. The method of claim 1, wherein the gas is a non-toxic gas.

5. The method of claim 4, wherein the non-toxic gas is $CO_2$.

6. The method of claim 1, wherein the liquid is forced through the channel at a rate in a range of about 0.01 nl/sec to about 100 microliters/sec.

7. The method of claim 6, wherein the gas is forced through the opening of the pressure chamber at a rate in the range of from about 50 m/sec to about 2000 m/sec.

8. The method of claim 1, wherein the liquid is fed through the channel at a rate in a range of about 1 nanoliter/sec to about 100 microliters/sec and further wherein the gas is forced through the opening of the pressure chamber at a rate in the range of from about 100 to 500 m/sec.

9. The method of claim 1, wherein the exit opening has a diameter in the range of from about 0.01 mm to about 0.4 mm, and
    wherein the exit opening of the feeding source is separated by a distance of from about 0.01 to about 2 mm from the exit orifice in the pressure chamber.

10. The method of claim 1, wherein the liquid formulation fed through the channel has a volume in the range of 5 microliters to 10,000 microliters.

11. A method of delivering aerosolized particles of a pharmaceutically active drug to a patient, comprising:
    feeding liquid formulation comprised of a pharmaceutically active drug through a channel of a liquid feeding source to an outlet having a diameter in a range of from about 0.002 mm to about 2 mm;
    feeding gas through an orifice having a diameter in a range of from about 0.002 mm to about 2 mm, the orifice being positioned downstream of the outlet in a direction aligned with a direction of flow out of the outlet as a liquid stream;
    wherein the feeding source outlet is separated by a distance of from about 0.002 mm to about 2 mm from the orifice; and
    wherein the liquid stream is accelerated by tangential viscous stress exerted by the gas on the liquid stream and the liquid and gas are each fed at a rate relative to each other so as to form aerosolized particles having a size in the range of about 0.1 micron to about 10 microns.

12. The method of claim 11, wherein gas is forced into an area around the feeding source outlet at a pressure in the range of 10 mBar above atmospheric pressure and further wherein the liquid has a viscosity in the range of from $10^{-4}$ to 1 kg/m/sec.

13. The method of claim 12, wherein gas is forced into an area around the feeding source outlet at a pressure below 50,000 mBar above atmospheric pressure.

14. The method of claim 12, wherein gas from the pressure chamber surrounds liquid exiting the feeding source outlet which liquid is drawn into the orifice concentrically being focused by the gas flowing out of the outlet, and further wherein the aerosolized particles formed are uniform in size to the extent of having a relative size standard deviation of 3 to 30%.

15. The method of claim 11, wherein the liquid formulation fed through the channel has a volume in the range of 5 microliters to 10,000 microliters.

* * * * *